United States Patent
Park et al.

(10) Patent No.: US 8,883,476 B2
(45) Date of Patent: Nov. 11, 2014

(54) **MUTANT OF PROPIONYL-COA TRANSFERASE FROM *CLOSTRIDIUM PROPIONICUM* AND PREPARING METHOD FOR PLA OR PLA COPOLYMER USING THE SAME**

(71) Applicants: Si Jae Park, Daejeon (KR); Taek Ho Yang, Daejeon (KR); Hye Ok Kang, Daejeon (KR); Sang Hyun Lee, Daejeon (KR); Eun Jung Lee, Daejeon (KR); Tae Wan Kim, Daejeon (KR)

(72) Inventors: Si Jae Park, Daejeon (KR); Taek Ho Yang, Daejeon (KR); Hye Ok Kang, Daejeon (KR); Sang Hyun Lee, Daejeon (KR); Eun Jung Lee, Daejeon (KR); Tae Wan Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 13/952,355

(22) Filed: Jul. 26, 2013

(65) Prior Publication Data
US 2014/0030774 A1    Jan. 30, 2014

Related U.S. Application Data

(62) Division of application No. 12/673,389, filed as application No. PCT/KR2008/004348 on Jul. 25, 2008, now Pat. No. 8,524,478.

(30) Foreign Application Priority Data

Aug. 14, 2007    (KR) .................. 10-2007-0081855

(51) Int. Cl.
| | | |
|---|---|---|
| *C12N 1/10* | (2006.01) | |
| *C12P 7/62* | (2006.01) | |
| *C07H 21/04* | (2006.01) | |
| *C12N 9/10* | (2006.01) | |

(52) U.S. Cl.
CPC ............... *C12P 7/625* (2013.01); *C12N 9/1048* (2013.01)
USPC ........................... 435/193; 435/135; 536/23.2

(58) Field of Classification Search
None
See application file for complete search history.

(56) References Cited

U.S. PATENT DOCUMENTS

2007/0277268 A1    11/2007    Cho et al.

FOREIGN PATENT DOCUMENTS

WO    WO 2006/126796    11/2006

OTHER PUBLICATIONS

Selmer et al. "Porpionate CoA-transferase from *Clostridium propionicum*, cloning of the gene and identification of glutamate 324 at the active site", Eur. J. Biochem, 269, 372-380, 2002.

Takase et al. "Enhanced systhesis of poly (3-hydroxybutyrate) in recombinant *Escherichia coli* by means of error-prone PCR mutagenesis, saturation mutagenesis, and In Vitro recombination of the Type II polyhydroxyalkanoate synthase gene", J. Biochem, vol. 133, pp. 139-145, 2003.

Selmer et al. "Propionate coA-transferase from *Clostridium propionicum*: cloning of the gene and identification of glutamate 324 at the active site" Eur. J. Biochem, vol. 269, pp. 370-380, 2002.

Takase et al., "Alteration of substrage chain-length specificity of Type II synthase for polyhydroxyalkanoate biosynthesis by in vitro evolution: in vivo and in vitro enzyme assays", Biomacromolecules, vol. 5, pp. 480-485, 2004.

Genbank Accession No. AJ276553, "*Clostridium propionicum* pct gene for propionate CoA-transferase and partial IcdB gene for lactoyl-CoA dehydratase beta-subunit", Mar. 9, 2000.

*Primary Examiner* — Iqbal H Chowdhury
(74) *Attorney, Agent, or Firm* — McKenna Long & Aldridge, LLP

(57) ABSTRACT

Provided is a mutant of propionyl-CoA transferase from *Clostridium propionicum* that can convert lactate into lactyl-CoA with high efficiency in a method of preparing a polylactate (PLA) or PLA copolymer using microorganisms. Unlike conventional propionyl-CoA transferase which is weakly expressed in *E. coli*, when a mutant of propiony-CoA transferase from *Clostridium propionicum* is introduced into recombinant *E. coli*, lactyl-CoA can be supplied very smoothly, thereby enabling highly efficient preparation of polylactate (PLA) and PLA copolymer.

1 Claim, 2 Drawing Sheets

SEQUENCE LISTING

<160> NUMBER OF SEQ ID NOS: 24

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
cgccggcagg cctgcagg                                               18

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ggcaggtcag cccatatgtc                                             20

<210> SEQ ID NO 3
<211> LENGTH: 1572

```
<212> TYPE: DNA
<213> ORGANISM: Clostridium propionicum
<220> FEATURE:
<223> OTHER INFORMATION: propionyl-CoA transferase

<400> SEQUENCE: 3
atgagaaagg ttcccattat taccgcagat gaggctgcaa agcttattaa agacggtgat      60
acagttacaa caagtggttt cgttggaaat gcaatccctg aggctcttga tagagctgta    120
gaaaaaagat tcttagaaac aggcgaaccc aaaaacatta cctatgttta ttgtggttct    180
caaggtaaca gagacggaag aggtgctgag cactttgctc atgaaggcct tttaaaacgt    240
tacatcgctg gtcactgggc tacagttcct gcttttggga aaatggctat ggaaaataaa    300
atggaagcat ataatgtatc tcagggtgca ttgtgtcatt tgttccgtga tatagcttct    360
cataagccag gcgtatttac aaaggtaggt atcggtactt tcattgaccc cagaaatggc    420
ggcggtaaag taatgatat taccaaagaa gatattgttg aattggtaga gattaagggt    480
caggaatatt tattctaccc tgcttttcct attcatgtag ctcttattcg tggtacttac    540
gctgatgaaa gcggaaatat cacatttgag aaagaagttg ctcctctgga aggaacttca    600
gtatgccagg ctgttaaaaa cagtggcggt atcgttgtag ttcaggttga agagtagta    660
aaagctggta ctcttgaccc tcgtcatgta aaagttccag gaatttatgt tgactatgtt    720
gttgttgctg acccagaaga tcatcagcaa tctttagatt gtgaatatga tcctgcatta    780
tcaggcgagc atagaagacc tgaagttgtt ggagaaccac ttcctttgag tgcaaagaaa    840
gttattggtc gtcgtggtgc cattgaatta gaaaaagatg ttgctgtaaa tttaggtgtt    900
ggtgcgcctg aatatgtagc aagtgttgct gatgaagaag gtatcgttga ttttatgact    960
ttaactgctg aaagtggtgc tattggtggt gttcctgctg gtggcgttcg ctttggtgct   1020
tcttataatg cggatgcatt gatcgatcaa ggttatcaat tcgattacta tgatggcggc   1080
ggcttagacc tttgctattt aggcttagct gaatgcgatg aaaaaggcaa tatcaacgtt   1140
tcaagatttg gccctcgtat cgctggttgt ggtggtttca tcaacattac acagaataca   1200
cctaaggtat tcttctgtgg tactttcaca gcaggtggct aaaggttaa aattgaagat   1260
ggcaaggtta ttattgttca agaaggcaag cagaaaaaat tcttgaaagc tgttgagcag   1320
attacattca atggtgacgt tgcacttgct aataagcaac aagtaactta tattacagaa   1380
agatgcgtat tccttttgaa ggaagatggt ttgcacttat ctgaaattgc acctggtatt   1440
gatttgcaga cacagattct tgacgttatg gattttgcac ctattattga cagagatgca   1500
aacggccaaa tcaaattgat ggacgctgct ttgtttgcag aaggcttaat gggtctgaag   1560
gaaatgaagt cc                                                       1572

<210> SEQ ID NO 4
<211> LENGTH: 1677
<212> TYPE: DNA
<213> ORGANISM: Artificial Sequence
<220> FEATURE:
<223> OTHER INFORMATION: PHA synthase gene

<400> SEQUENCE: 4
atgagtaaca agagtaacga tgagttgaag tatcaagcct ctgaaaacac cttggggctt     60
aatcctgtcg ttgggctgcg tggaaaggat ctactggctt ctgctcgaat ggtgcttagg    120
caggccatca gcaaccggt gcacagcgtc aacatgtcg cgcactttgg tcttgaactc    180
aagaacgtac tgctgggtaa atccgggctg caaccgacca gcgatgaccg tcgcttcgcc    240
```

-continued

| | |
|---|---|
| gatccggcct ggagccagaa cccgctctat aaacgttatt tgcaaaccta cctggcgtgg | 300 |
| cgcaaggaac tccacgactg gatcgatgaa agtaacctcg cccccaagga tgtggcgcgt | 360 |
| gggcacttcg tgatcaacct catgaccgat gcgatggcgc cgaccaacac cgcggccaac | 420 |
| ccggcggcag tcaaacgctt ttttgaaacc ggtggcaaaa gctgctcga cggcctctcg | 480 |
| cacctggcca aggatctggt acacaacggc ggcatgccga gccaggtcaa catgggtgca | 540 |
| ttcgaggtcg gcaagagcct gggcgtgacc gaaggcgcgg tggtgtttcg caacgatgtg | 600 |
| ctggaactga tccagtacaa gccgaccacc gagcaggtat acgaacgccc gctgctggtg | 660 |
| gtgccgccgc agatcaacaa gttctacgtt ttcgacctga gcccggacaa gagcctggcg | 720 |
| cggttctgcc tgcgcaacaa cgtgcaaacg ttcatcgtca gctggcgaaa tcccaccaag | 780 |
| gaacagcgag agtggggcct gtcgacctac atcgaagccc tcaaggaagc ggttgacgtc | 840 |
| gttaccgcga tcaccggcag caaagacgtg aacatgctcg gggcctgctc cggcggcatc | 900 |
| acttgcactg cgctgctggg ccattacgcg gcgattggcg aaaacaaggt caacgccctg | 960 |
| accttgctgg tgaccgtgct tgataccacc ctcgacagcg acgtcgccct gttcgtcaat | 1020 |
| gaacagaccc ttgaagccgc caagcgccac tcgtaccagg ccggcgtact ggaaggccgc | 1080 |
| gacatggcga aggtcttcgc ctggatgcgc cccaacgatc tgatctggaa ctactgggtc | 1140 |
| aacaattacc tgctaggcaa cgaaccgccg gtgttcgaca tcctgttctg gaacaacgac | 1200 |
| accacacggt tgcccgcggc gttccacggc gacctgatcg aactgttcaa aaataaccca | 1260 |
| ctgattcgcc cgaatgcact ggaagtgtgc ggcacccccca tcgacctcaa gcaggtgacg | 1320 |
| gccgacatct tttccctggc cggcaccaac gaccacatca ccccgtggaa gtcctgctac | 1380 |
| aagtcggcgc aactgtttgg cggcaacgtt gaattcgtgc tgtcgagcag cgggcatatc | 1440 |
| atgagcatcc tgaacccgcc gggcaatccg aaatcgcgct acatgaccag caccgaagtg | 1500 |
| gcggaaaatg ccgatgaatg gcaagcgaat gccaccaagc atacagattc ctggtggctg | 1560 |
| cactggcagg cctggcaggc ccaacgctcg ggcgagctga aaaagtcccc gacaaaactg | 1620 |
| ggcagcaagg cgtatccggc aggtgaagcg gcgccaggca cgtacgtgca cgaacgg | 1677 |

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gagagacaat caaatcatga gtaacaagag taacg                              35

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
cactcatgca agcgtcaccg ttcgtgcacg tac                                33

<210> SEQ ID NO 7
<211> LENGTH: 20
<212> TYPE: DNA
<213> ORGANISM: Artificial Sequence
<220> FEATURE:
<223> OTHER INFORMATION: Primer

```
<400> SEQUENCE: 7
atgcccggag ccggttcgaa                                               20

<210> SEQ ID NO 8
<211> LENGTH: 35
<212> TYPE: DNA
<213> ORGANISM: Artificial Sequence
<220> FEATURE:
<223> OTHER INFORMATION: Primer

<400> SEQUENCE: 8
cgttactctt gttactcatg atttgattgt ctctc                              35

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
gagagacaat caaatcatga gtaacaagag taacg                              35

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
cactcatgca agcgtcaccg ttcgtgcacg tac                                33

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
gtacgtgcac gaacggtgac gcttgcatga gtg                                33

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
aacgggaggg aacctgcagg                                               20

<210> SEQ ID NO 13
<211> LENGTH: 1677
<212> TYPE: DNA
<213> ORGANISM: Pseudomonas sp. 6-19
<220> FEATURE:
<223> OTHER INFORMATION: KCTC 11027BP

<400> SEQUENCE: 13
atgagtaaca agagtaacga tgagttgaag tatcaagcct ctgaaaacac cttggggctt    60
aatcctgtcg ttgggctgcg tggaaaggat ctactggctt ctgctcgaat ggtgcttagg   120
```

-continued

| | |
|---|---|
| caggccatca agcaaccggt gcacagcgtc aaacatgtcg cgcactttgg tcttgaactc | 180 |
| aagaacgtac tgctgggtaa atccgggctg caaccgacca gcgatgaccg tcgcttcgcc | 240 |
| gatccggcct ggagccagaa cccgctctat aaacgttatt tgcaaaccta cctggcgtgg | 300 |
| cgcaaggaac tccacgactg gatcgatgaa agtaacctcg cccccaagga tgtggcgcgt | 360 |
| gggcacttcg tgatcaacct catgaccgaa gcgatggcgc cgaccaacac cgcggccaac | 420 |
| ccggcggcag tcaaacgctt ttttgaaacc ggtggcaaaa gcctgctcga cggcctctcg | 480 |
| cacctggcca aggatctggt acacaacggc ggcatgccga gccaggtcaa catgggtgca | 540 |
| ttcgaggtcg gcaagagcct gggcgtgacc gaaggcgcgg tggtgtttcg caacgatgtg | 600 |
| ctggaactga tccagtacaa gccgaccacc gagcaggtat acgaacgccc gctgctggtg | 660 |
| gtgccgccgc agatcaacaa gttctacgtt tcgacctga gcccggacaa gagcctggcg | 720 |
| cggttctgcc tgcgcaacaa cgtgcaaacg ttcatcgtca gctggcgaaa tcccaccaag | 780 |
| gaacagcgag agtggggcct gtcgacctac atcgaagccc tcaaggaagc ggttgacgtc | 840 |
| gttaccgcga tcaccggcag caaagacgtg aacatgctcg gggcctgctc cggcggcatc | 900 |
| acttgcactg cgctgctggg ccattacgcg gcgattggcg aaaacaaggt caacgccctg | 960 |
| accttgctgg tgagcgtgct tgataccacc ctcgacagcg acgtcgccct gttcgtcaat | 1020 |
| gaacagaccc ttgaagccgc caagcgccac tcgtaccagg ccggcgtact ggaaggccgc | 1080 |
| gacatggcga aggtcttcgc ctggatgcgc cccaacgatc tgatctggaa ctactgggtc | 1140 |
| aacaattacc tgctaggcaa cgaaccgccg gtgttcgaca tcctgttctg gaacaacgac | 1200 |
| accacacggt tgcccgcggc gttccacggc gacctgatcg aactgttcaa aaataaccca | 1260 |
| ctgattcgcc cgaatgcact ggaagtgtgc ggcaccccca tcgacctcaa gcaggtgacg | 1320 |
| gccgacatct tttccctggc cggcaccaac gaccacatca ccccgtggaa gtcctgctac | 1380 |
| aagtcggcgc aactgtttgg cggcaacgtt gaattcgtgc tgtcgagcag cgggcatatc | 1440 |
| cagagcatcc tgaaccccgcc gggcaatccg aaatcgcgct acatgaccag caccgaagtg | 1500 |
| gcggaaaatg ccgatgaatg caagcgaat gccaccaagc atacagattc ctggtggctg | 1560 |
| cactggcagg cctggcaggc ccaacgctcg ggcgagctga aaaagtcccc gacaaaactg | 1620 |
| ggcagcaagg cgtatccggc aggtgaagcg gcgccaggca cgtacgtgca cgaacgg | 1677 |

<210> SEQ ID NO 14
<211> LENGTH: 559
<212> TYPE: PRT
<213> ORGANISM: Pseudomonas sp. 6-19
<220> FEATURE:
<223> OTHER INFORMATION: KCTC 11027BP

<400> SEQUENCE: 14

Met Ser Asn Lys Ser Asn Asp Glu Leu Lys Tyr Gln Ala Ser Glu Asn
 1               5                   10                  15

Thr Leu Gly Leu Asn Pro Val Val Gly Leu Arg Gly Lys Asp Leu Leu
                20                  25                  30

Ala Ser Ala Arg Met Val Leu Arg Gln Ala Ile Lys Gln Pro Val His
            35                  40                  45

Ser Val Lys His Val Ala His Phe Gly Leu Glu Leu Lys Asn Val Leu
        50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

```
Tyr Leu Ala Trp Arg Lys Glu Leu His Asp Trp Ile Asp Glu Ser Asn
                100                 105                 110

Leu Ala Pro Lys Asp Val Ala Arg Gly His Phe Val Ile Asn Leu Met
            115                 120                 125

Thr Glu Ala Met Ala Pro Thr Asn Thr Ala Ala Asn Pro Ala Ala Val
130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
            420                 425                 430

Pro Ile Asp Leu Lys Gln Val Thr Ala Asp Ile Phe Ser Leu Ala Gly
        435                 440                 445

Thr Asn Asp His Ile Thr Pro Trp Lys Ser Cys Tyr Lys Ser Ala Gln
450                 455                 460

Leu Phe Gly Gly Asn Val Glu Phe Val Leu Ser Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
            500                 505                 510
```

Lys His Thr Asp Ser Trp Trp Leu His Trp Gln Ala Trp Gln Ala Gln
            515                 520                 525

Arg Ser Gly Glu Leu Lys Lys Ser Pro Thr Lys Leu Gly Ser Lys Ala
        530                 535                 540

Tyr Pro Ala Gly Glu Ala Ala Pro Gly Thr Tyr Val His Glu Arg
545                 550                 555

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
ctgaccttgc tggtgaccgt gcttgatacc acc                           33

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
ggtggtatca agcacggtca ccagcaaggt cag                           33

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
cgagcagcgg gcatatcatg agcatcctga acccgc                        36

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
gcgggttcag gatgctcatg atatgcccgc tgctcg                        36

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
atcaacctca tgaccgatgc gatggcgccg acc                           33

<210> SEQ ID NO 20
<211> LENGTH: 33
<212> TYPE: DNA
<213> ORGANISM: Artificial Sequence
<220> FEATURE:
<223> OTHER INFORMATION: Primer

<400> SEQUENCE: 20

-continued

```
ggtcggcgcc atcgcatcgg tcatgaggtt gat                                33
```

<210> SEQ ID NO 21
<211> LENGTH: 39
<212> TYPE: DNA
<213> ORGANISM: Artificial Sequence
<220> FEATURE:
<223> OTHER INFORMATION: Primer

<400> SEQUENCE: 21

```
ggaattcatg agaaaggttc ccattattac cgcagatga                          39
```

<210> SEQ ID NO 22
<211> LENGTH: 46
<212> TYPE: DNA
<213> ORGANISM: Artificial Sequence
<220> FEATURE:
<223> OTHER INFORMATION: Primer

<400> SEQUENCE: 22

```
gctctagatt aggacttcat ttccttcaga cccattaagc cttctg                  46
```

<210> SEQ ID NO 23
<211> LENGTH: 32
<212> TYPE: DNA
<213> ORGANISM: Artificial Sequence
<220> FEATURE:
<223> OTHER INFORMATION: Primer

<400> SEQUENCE: 23

```
aggcctgcag gcggataaca atttcacaca gg                                 32
```

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24

```
gcccatatgt ctagattagg acttcatttc c                                  31
```

MUTANT OF PROPIONYL-CoA TRANSFERASE FROM *CLOSTRIDIUM PROPIONICUM* AND PREPARING METHOD FOR PLA OR PLA COPOLYMER USING THE SAME

This application is a Divisional of U.S. patent application Ser. No. 12/673,389, filed on Feb. 12, 2010, which is a National Stage Application of PCT/KR2008/004348, filed on Jul. 25, 2008 and claims the benefit of Korean Patent Application No. 10-2007-0081855, filed Aug. 14, 2007, the disclosures of which are incorporated by reference in their entirety.

TECHNICAL FIELD

The present invention relates to a mutant of propionyl-CoA transferase from *Clostridium propionicum*, which can convert lactate into lactyl-CoA with high efficiency in a method of preparing a polylactate (PLA) or PLA copolymer using microorganisms.

BACKGROUND ART

Polylactate (PLA) is a typical biodegradable polymer derived from lactate that is highly applicable commercially and biomedically. Although preparation of PLA presently involves polymerization of lactate produced by fermenting microorganisms, only PLA with a low molecular weight of about 1000 to 5000 daltons is obtained by direct polymerization of lactate. In order to synthesize PLA with a molecular weight of 100,000 daltons or higher, PLA with a low molecular weight obtained by direct polymerization of lactate may be polymerized using a chain coupling agent. In this method, however, the entire process becomes complicated due to addition of an organic solvent or a chain coupling agent, which is not easy to remove. A presently commercially available process of preparing high-molecular weight PLA may include converting lactate into lactide and synthesizing PLA using ring-opening polycondensation of lactide rings.

When PLA is synthesized by chemical synthesis of lactate, a PLA homopolymer is easily obtained, but a PLA copolymer composed of various types of monomers is difficult to synthesize and commercially unavailable.

Meanwhile, polyhydroxyalkanoate (PHA) is polyester stored by microorganisms as energy or a carbon source when there are excessive carbon sources and a lack of other nutrients, such as phosphorus (P), nitrogen (N), magnesium (Mg) and oxygen (O), etc. Since PHA has similar physical properties to a conventional synthetic polymer from petroleum and exhibits complete biodegradability, it is being recognized as a substitute for conventional synthetic plastics.

In order to produce PHA using microorganisms, an enzyme for converting microbial metabolic products into a PHA monomer, and PHA synthase for synthesizing a PHA polymer using the PHA monomer, are needed. When synthesizing PLA and PLA copolymer using microorganisms, the same system is required, and an enzyme for providing lactyl-CoA is needed in addition to an enzyme for providing hydroxyacyl-CoA, which is an original substrate of PHA synthase.

Therefore, in order to provide lactyl-CoA, the present inventors used propionyl-CoA transferase from *Clostridium propionicum* and a mutant of PHA synthase from *Pseudomonas* sp. 6-19 using the propionyl-CoA transferase as a substrate, thus could successfully synthesize PLA and PLA copolymer as disclosed in Korean Patent Application NO. 10-2006-0116234.

However, it was reported that when propionyl-CoA transferase from *Clostridium propionicum*, which is an enzyme for supplying lactyl-CoA, is highly expressed in *E. coli* by a very potent promoter, serious metabolic disorder occurs, thus inhibiting cell growth (Selmer et al. reported in Eur. J. Biochem. 269:372, 2002). Also, since the codon usage of a gene for encoding propionyl-CoA transferase from *Clostridium propionicum* is quite different from that of *E. coli*, it may be very difficult to normally express propionyl-CoA transferase. Accordingly, in order to synthesize PLA and PLA copolymer more efficiently than conventional systems, it is very important to introduce propionyl-CoA transferase, which smoothly provides lactyl-CoA and is expressed enough not to greatly inhibit cell growth.

DISCLOSURE

Technical Problem

The present invention is directed to a method of preparing a polylactate (PLA) or PLA copolymer with high efficiency by providing a monomer-supplying enzyme capable of efficiently supplying lactyl-CoA.

Technical Solution

The present inventors found that when a mutant of propionyl-CoA transferase from *Clostridium propionicum* is used, a PLA or PLA copolymer can be prepared with high efficiency by efficiently supplying lactyl-CoA without greatly inhibiting cell growth. This led them to complete the present invention.

Accordingly, the present invention provides a mutant of propionyl-CoA transferase functioning as a lactyl-CoA-supplying enzyme, which has a gene sequence of SEQ ID NO: 3, in which T78C, T669C, A1125G and T1158C are mutated, and a gene encoding the mutant.

The present invention also provides a mutant of propionyl-CoA transferase functioning as a lactyl-CoA-supplying enzyme, which has a gene sequence of SEQ ID NO: 3 in which A1200G is mutated, and a gene encoding the mutant.

The present invention also provides a mutant of propionyl-CoA transferase functioning as a lactyl-CoA-supplying enzyme, which has a gene sequence of SEQ ID NO: 3 in which A1200G is mutated and an amino acid sequence corresponding to SEQ ID NO: 3 in which Gly335Asp is mutated, and a gene encoding the mutant.

The present invention also provides a mutant of propionyl-CoA transferase functioning as a lactyl-CoA-supplying enzyme, which has a gene sequence of SEQ ID NO: 3 in which T669C, A1125G and T1158C are mutated, and an amino acid sequence corresponding to SEQ ID NO: 3 in which Asp65Gly is mutated, and a gene encoding the mutant.

The present invention also provides a mutant of propionyl-CoA transferase functioning as a lactyl-CoA-supplying enzyme, which has a gene sequence of SEQ ID NO: 3 in which T669C, A1125G and T1158C are mutated and an amino acid sequence corresponding to SEQ ID NO: 3 in which Asp65Asn is mutated, and a gene encoding the mutant.

The present invention also provides a mutant of propionyl-CoA transferase functioning as a lactyl-CoA-supplying enzyme, which has a gene sequence of SEQ ID NO: 3 in which T669C, A1125G and T1158C are mutated and an amino acid sequence corresponding to SEQ ID NO: 3 in which Thr199Ile is mutated, and a gene encoding the mutant.

The present invention also provides a mutant of propionyl-CoA transferase functioning as a lactyl-CoA-supplying enzyme, which has a gene sequence of SEQ ID NO: 3 in which A1200G is mutated and an amino acid sequence corresponding to SEQ ID NO: 3 in which Ala243Thr is mutated, and a gene encoding the mutant.

The present invention also provides a mutant of propionyl-CoA transferase functioning as a lactyl-CoA-supplying enzyme, which has a gene sequence of SEQ ID NO: 3 in which A1200G is mutated and an amino acid sequence corresponding to SEQ ID NO: 3 in which Asp257Asn is mutated, and a gene encoding the mutant.

The present invention also provides a mutant of propionyl-CoA transferase functioning as a lactyl-CoA-supplying enzyme, which has a gene sequence of SEQ ID NO: 3 in which T78C, T669C, A1125G and T1158C are mutated and an amino acid sequence corresponding to SEQ ID NO: 3 in which Val193Ala is mutated, and a gene encoding the mutant.

The present invention also provides a recombinant vector for synthesizing a polylactate (PLA) or PLA copolymer, which contains any one of the above-described genes.

Preferably, the recombinant vector for synthesizing a polylactate (PLA) or PLA copolymer contains any one of the above-described genes encoding a mutant of propionyl-CoA transferase and a polyhydroxyalkanoate (PHA) synthase gene (phaC1$_{Ps6-19}$300) of SEQ ID NO: 4, which is capable of synthesizing a PLA or PLA copolymer using lactyl-CoA as a substrate.

The present invention also provides a cell or plant transformed with one of the above-described recombinant vectors. In this case, a cell or plant obtained by transforming a cell or plant without a gene of propionyl-CoA transferase with one of the above-described recombinant vectors is also within the scope of the present invention.

The present invention also provides a method of preparing a polylactate (PLA) or PLA copolymer, comprising culturing or growing the above-described cell or plant is cultured or grown. In order to prepare a PLA copolymer, culturing or growing the cell or plant may be performed in an environment containing hydroxyalkanoate. The hydroxyalkanoate may be at least one selected from the group consisting of 3-hydroxybutyrate, 3-hydroxyvalerate, 4-hydroxybutyrate, medium chain-length (D)-3-hydroxycarboxylic acid with 6 to 14 carbon atoms, 2-hydroxypropionic acid, 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methylester, 3-hydroxyadipinic acid-methylester, 3-hydroxysuberic acid-methyl ester, 3-hydroxyazelaic acid-methyl ester, 3-hydroxysebacic acid-methylester, 3-hydroxysuberic acid-ethylester, 3-hydroxysebacic acid-ethylester, 3-hydroxypimelic acid-propylester, 3-hydroxysebacic acid-benzylester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid, and 3-hydroxy-2,6-dimethyl-5-heptenoic acid. However, the present invention is not limited thereto.

The hydroxyalkanoate may be at least one selected from the group consisting of 3-hydroxybutyrate, 4-hydroxybutyrate, 2-hydroxypropionic acid, 3-hydroxypropionic acid, medium chain-length (D)-3-hydroxycarboxylic acid with 6 to 14 carbon atoms, 3-hydroxyvalerate, 4-hydroxyvaleric acid, and 5-hydroxyvaleric acid. More preferably, but not necessarily, the hydroxyalkanoate may be 3-hydroxybutyrate (3-HB) (refer to FIG. 1).

Accordingly, the PLA or PLA copolymer of the present invention may be polylactate, poly(hydroxyalkanoate-co-3-lactate), poly(hydroxyalkanoate-co-hydroxyalkanoate-co-lactate), poly(hydroxyalkanoate-co-hydroxyalkanoate-co-polyhydroxyalkanoate-co-lactate) and so on, but the present invention is not limited thereto.

For example, the PLA copolymer may be poly(4-hydroxybutyrate-co-lactate), poly(4-hydroxybutyrate-co-3-hydroxypropionate-co-lactate), poly(3-hydroxybutyrate-co-4-hydroxybutyrate-co-lactate), poly(3-hydroxybutyrate-co-3-hydroxypropionate-co-4-hydroxybutyrate-co-lactate), poly (medium chain length (MCL) 3-hydroxyalkanoate-co-lactate), poly(3-hydroxybutyrate-co-MCL 3-hydroxyalkanoate-co-lactate), poly(3-hydroxybutyrate-co-3-hydroxyvalerate-co-lactate), poly(3-hydroxybutyrate-co-3-hydroxypropionate-co-lactate), poly(3-hydroxypropionate-co-lactate) and so on, but the present invention is not limited thereto.

In the present invention, a vector refers to a DNA construct containing a DNA sequence that is operably linked to a suitable control sequence capable of expressing DNA in an appropriate host. The vector may be a plasmid, a phage particle, or a simply latent genome insert. When the vector is transformed into an appropriate host, the vector is capable of replicating or functioning irrespective of a host genome or, in some cases, being integrated with the genome itself. Since a plasmid is presently the most general type of vectors, the plasmid and vector may sometimes be used interchangeably in the present invention. However, the present invention includes other types of vectors known to one skilled in the art or those with equivalent functions.

The term "expression control sequence" means a DNA sequence essential for expression of an operably linked coding sequence in a specific host. The control sequence includes a promoter required for transcription, an arbitrary operator sequence for controlling the transcription, a sequence for coding an appropriate mRNA ribosome binding site (RBS), and a sequence for controlling termination of transcription and translation. For example, a control sequence suitable for a prokaryote includes a promoter, a random operator sequence, and an RBS. A control sequence suitable for a eukaryotic cell includes a promoter, a polyadenylation signal, and an enhancer. The most important factor that affects the expression amount of a gene in a plasmid is a promoter. A SRα promoter or a cytomegalovirus promoter may be used as a high-expression promoter.

In order to express a DNA sequence of the present invention, any one of various expression control sequences may be used for a vector. The expression control sequence may be, for example, early and late promoters of SV40 or adenovirus, the lac system, the trp system, the tac system, the trc system, T3 and T7 promoters, the major operator and promoter regions of phage λ, the control region of fd code protein, the promoters of 3-phosphoglycerate kinase or other glycolytic enzymes, the promoters of phosphatase, for example, Pho5, α-mating systems of yeast, other sequences with different configurations or derivations known to control expression of a prokaryotic or eukaryotic cell or their viruses, and various combinations thereof.

When a nucleic acid is disposed in a functional relationship with other nucleic acid sequence, it is operably linked to the nucleic acid sequence. An appropriate molecule (e.g., a transcription-activating protein) may be a gene and control sequence(s) that are linked in such a manner as to enable expression of the gene when it couple with the control sequence(s). For example, DNA of a pre-sequence or a secretory leader is operably linked to DNA of polypeptide when it is expressed as a pre-protein that participates in secretion of polypeptide; a promoter or enhancer is operably linked to a coding sequence when it affects transcription of the coding sequence; an RBS is operably linked to a coding sequence when it affects transcription of the coding sequence; or the RBS is operably linked to the coding sequence when it is disposed to facilitate translation. In general, "operably linked" means that DNA sequences being linked are contiguous, and in case of the secretory leader, contiguous and in a reading frame. However, an enhancer does not have to contact a coding sequence. Linkage between sequences may be performed by ligation in a convenient restriction enzyme site. However, when there is no restriction enzyme site, a synthetic oligonucleotide adaptor or linker may be used according to an ordinary method.

In the present invention, the term "expression vector" refers a recombinant carrier into which heterologous DNA fragments are inserted, wherein the DNA fragment is generally a double-strand DNA fragment. Here, heterologous DNA means hetero-type DNA that is not naturally found in a host cell. Once the expression vector is incorporated with a host cell, it can be replicated irrespective of host genomic DNA to generate several copies and their inserted (heterologous) DNAs.

As is known to one skilled in the art, in order to raise an expression level of a transfected gene in a host cell, the corresponding gene must be operably linked to an expression control sequence that performs transcription and translation functions in a selected expression host. Preferably, the expression control sequence and the gene are included in a single expression vector comprising both a bacterial selectable marker and a replication origin. When an expression host is a eukaryotic cell, the expression vector must further include an expression marker useful in the eukaryotic expression host.

In the present invention, various vectors including a plasmid vector, a bacteriophage vector, a cosmid vector, and a yeast artificial chromosome (YAC) vector may be adopted as recombinant vectors. For the purpose of the present invention, a plasmid vector may be used as a recombination vector. A typical plasmid vector that serves the purpose of the invention includes (a) a replication origin that allows efficient replication such that each host cell includes several hundred plasmid vectors, (b) an antibiotic-resistance gene that allows selection of a host cell of which is transformed with a plasmid vector, and (c) a restriction enzyme cleavage site in which a foreign DNA fragment may be inserted. Even if there is no appropriate restriction enzyme cleavage site, a vector may be easily ligated with foreign DNA by an ordinary method using a synthetic oligonucleotide adaptor or linker.

A recombinant vector according to the present invention may be transformed into an appropriate host cell using an ordinary method. The host cell may be bacteria, yeast, fungi and so on, but the present invention is not limited thereto. Preferably, the host cell may be a prokaryotic cell, for example, *E. coli*. Examples of appropriate prokaryotic host cells may include *E. coli* strain JM109, *E. coli* strain DH5a, *E. coli* strain JM101, *E. coli* K12 strain 294, *E. coli* strain W3110, *E. coli* strain X1776, *E. coli* XL-1Blue (Stratagene), *E. coli* B, etc. However, *E. coli* strains, such as FMB101, NM522, NM538, and NM539, and other prokaryotic species and genera may be also used. In addition to the above-described *E. coli*, *Agrobacterium* sp. strains such as *Agrobacterium* A4, bacilli such as *Bacillus subtilis*, other enterobacteria such as *Salmonella typhimurium* or *Serratia marcescens*, and various *Pseudomonas* sp. strains may be used as host cells. However, the present invention is not limited to the above-described examples.

Also, the transformation of a eukaryotic cell may be easily accomplished using a calcium chloride method described in section 1.82, supra by Sambrook et al. Alternatively, electroporation may be employed to transform theses cells (Neumann et al., EMBO J., 1:841 (1982)).

In order to prepare a plant containing a gene of a converting enzyme and a gene of a synthase according to the present invention, transfection of the plant may be performed by an ordinary method using *Agrobacterium*, a virus vector, etc. For example, an *Agrobacterium* sp. microbe is transformed with a recombinant vector containing the gene according to the present invention, and the transformed *Agrobacterium* sp. microbe may infect tissue of a target plant, thereby obtaining a transfected plant. More specifically, preparation of a transfected plant may include (a) pre-culturing an explant of a target plant and co-culturing the explant with transformed *Agrobacterium* to transfect the explant; (b) culturing the transfected explant in a callus-inducing medium to obtain a callus; and (c) cutting and culturing the obtained callus in a shoot-inducing medium to obtain a shoot.

In the present invention, the term "explant" refers to a tissue fragment cut off from a plant and includes a cotyledon or a hypocotyl. The cotyledon or hypocotyl may be used as an explant of a plant used for the method of the present invention. The cotyledon, which is obtained by disinfecting and cleaning a seed of a plant and germinating the seed in a Murashige and Skoog (MS) medium, may be preferably used.

In the present invention, target plants to be transfected may be tobaccos, tomatoes, red peppers, beans, rice plants, corns, etc., but the present invention is not limited thereto. Also, it is known to one skilled in the art that even if a plant used for transformation is sexually reproducible, it can be asexually reproduced by tissue culture, etc.

Advantageous Effects

As explained above, it was conventionally difficult to express propionyl-CoA transferase in *E. coli*, thereby precluding efficient supply of lactyl-CoA. However, according to the present invention, a mutant of propiony-CoA transferase from *Clostridium propionicum* is introduced into recombinant *E. coli* to facilitate supply of lactyl-CoA, thereby preparing polylactate (PLA) and PLA copolymer with high efficiency.

MODE FOR INVENTION

Figure 1:
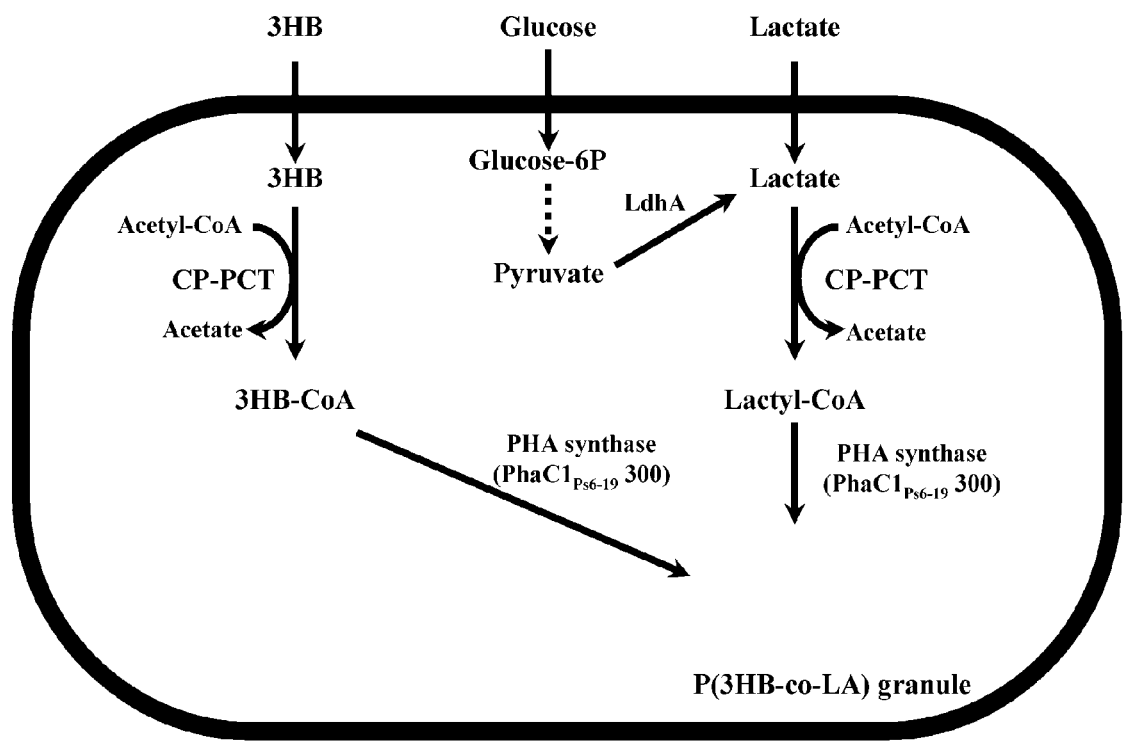
FIG. 1 is a schematic diagram of a intracellular synthesis pathway of lactate copolymer (poly(3HB-co-lactate)) using glucose, 3HB and lactate.

Hereinafter, the present invention will be described in detail through examples. It is obvious to one skilled in the art that the examples is provided only to explain the present invention in detail, the present invention is not limited to the examples According to a previous invention of the present inventors disclosed in Korean Patent Application No 10-2006-0116234, in order to provide lactyl-CoA that is a monomer required for synthesis of polylactate (PLA) and PLA copolymer, an operon-type constant expression system in which propionyl-CoA transferase from *Clostridium propionicum* (CP-PCT) and polyhydroxyalkanoate (PHA) synthase are expressed together was constructed as will now be described in more detail.

Example 1-1

Cloning of a PHA Synthase Gene from *Pseudomonas* Sp. 6-19 and Preparation of Expression Vector In order to separate PHA synthase ((phaC1$_{Ps6-19}$) gene from *Pseudomonas* sp. 6-19 (KCTC 11027BP) used in the present invention, the total DNA of *Pseudomonas* sp. 6-19 was extracted, primers having base sequences of SEQ ID NOs: 5 and 6 were prepared based on a sequence of the phaC1$_{Ps6-19}$ gene (Ae-jin Song, Master's Thesis, Department of Chemical and Biomolecular Engineering, KAIST, 2004), and polymerase chain reaction (PCR) was performed to obtain the phaC1$_{Ps6-19}$ gene.

SEQ ID NO: 5:
5'-GAG AGA CAA TCA AAT CAT GAG TAA CAA GAG

TAA CG-3'

SEQ ID NO: 6:
5'-CAC TCA TGC AAG CGT CAC CGT TCG TGC ACG

TAC-3'

As a result of performing Agarose gel electrophoresis of the PCR product, a 1.7-kbp gene fragment corresponding to phaC1$_{Ps6-19}$ gene was confirmed.

A DNA fragment containing a PHB-producing operon from *Ralstonia eutropha* H16 was cut with BamHI/EcoRI from a pSYL105 vector (Lee et al., Biotech. Bioeng., 1994, 44:1337-1347), and inserted into a BamHI/EcoRI recognition site of pBluescript II (Stratagene), thereby preparing a pReCAB recombinant vector.

It is known that the pReCAB vector in which PHA synthase (phaC$_{RE}$) and monomer-supplying enzymes (phaA$_{RE}$ and phaB$_{RE}$) are constantly expressed by a PHB operon promoter, is also effectively operated in *E. coli*. (Lee et al., Biotech. Bioeng., 1994, 44:1337-1347). The pReCAB vector was cut with BstBI/SbfI to remove *R. eutropha* H16 PHA synthase (phaC$_{RE}$), and the phaC1$_{Ps6-19}$ gene was inserted into a BstBI/SbfI recognition site, thereby preparing a pPs619C1-ReAB recombinant vector.

In order to produce a phaC1$_{Ps6-19}$ synthase gene fragment having only a BstBI/SbfI recognition site on either end, an endogenous BstBI site was removed using site-directed mutagenesis (SDM) without change of amino acids, and an overlapping PCR was performed using primers of SEQ ID NOs: 7 and 8, SEQ ID NOs:9 and 10, and SEQ ID NOs: 11 and 12 in order to add the BstBI/SbfI recognition site.

SEQ ID NO: 7:
5'-ATG CCC GGA GCC GGT TCG AA-3'

SEQ ID NO: 8:
5'-CGT TAC TCT TGT TAC TCA TGA TTT GAT GTT CTC

TC-3'

SEQ ID NO: 9:
5'-GAG AGA CAA TCA AAT CAT GAG TAA CAA GAG

TAA CG-3'

SEQ ID NO: 10:
5'-CAC TCA TGC AAG CGT CAC CGT TCG TGC ACG

TAC-3'

SEQ ID NO: 11:
5'-GTA CGT GCA CGA ACG GTG ACG CTT GCA TGA

GTG-3'

SEQ ID NO: 12:
5'-AAC GGG AGG GAA CCT GCA GG-3'

The base sequence of the phaC1$_{Ps6-19}$ gene of the prepared pPs619C1-ReAB recombinant vector was confirmed by sequencing and represented by SEQ ID NO: 13, and the amino acid sequence coded thereby was represented by SEQ ID NO: 14.

The gene sequence similarity analysis results show that the phaC1$_{Ps6-19}$ gene has a homology of 84.3% with phaC1 from *Pseudomonas* sp. strain 61-3 (Matsusaki et al., *J. Bacteriol.*, 180:6459, 1998) and an amino-acid sequence homology of 88.9%. Thus, it was confirmed that the two synthases were very similar enzymes. As a result, it was confirmed that the phaC1$_{Ps6-19}$ synthase obtained according to the invention was a Type II PHA synthase.

Example 1-2

Preparation of a Substrate-Specific Mutant of a PHA Synthase from *Pseudomonas* sp. 6-19

Among various kinds of PHA synthases, a Type II PHA synthase is known as a medium-chain-length PHA (MCL-PHA) synthase for polymerizing a substrate having relatively many carbon atoms, and the MCL-PHA synthase is expected to be very applicable to production of a PLA copolymer. Although phaC1 synthase from *Pseudomonas* sp. 61-3, which has a high homology with the phaC1$_{Ps6-19}$ synthase obtained according to the present invention, is the Type II synthase, it was reported that the phaC1 synthase had a relatively wide range of substrate specificity (Matsusaki et al., *J. Bacteriol.*, 180:6459, 1998), and results of research in a mutant suitable for production of short-chain-length PHA (SCL-PHA) were reported (Takase et al., *Biomacromolecules*, 5:480, 2004). Based on the above, the present inventors found three amino-acid sites affecting SCL activation via amino-acid sequence arrangement analysis, and prepared mutants of phaC1$_{Ps6-19}$ synthase by an SDM method using primers of SEQ ID NOs: 15 to 20 as shown in Table 1.

TABLE 1

| Recombinant vector | Nucleic acid substitution | Amino acid substitution | Primer |
|---|---|---|---|
| pPs619C1200-ReAB | AGC→ACC | S325T | SEQ ID NOs: 15/16 |
|  | CAG→ATG | Q481M | SEQ ID NOs: 17/18 |
| pPs619C1300-ReAB | GAA→GAT | E130D | SEQ ID NOs: 19/20 |
|  | AGC→ACC | S325T | SEQ ID NOs: 15/16 |
|  | CAG→ATG | Q481M | SEQ ID NOs: 17/18 |

SEQ ID NO: 15:
5'-CTG ACC TTG CTG GTG ACC GTG CTT GAT ACC ACC-3'

SEQ ID NO: 16:
5'-GGT GGT ATC AAG CAC GGT CAC CAG CAA GGT CAG-3'

SEQ ID NO: 17:
5'-CGA GCA GCG GGC ATA TC A TGA GCA TCC TGA ACC CGC-3'

SEQ ID NO: 18:
5'-GCG GGT TCA GGA TGC TCA TGA TAT GCC CGC TGC TCG-3'

SEQ ID NO: 19:
5'-ATC AAC CTC ATG ACC GAT GCG ATG GCG CCG ACC-3'

SEQ ID NO: 20:
5'-GGT CGG CGC CAT CGC ATC GGT CAT GAG GTT GAT-3'

Example 1-3

Preparation and Screening of a Library of a Mutant of Propionyl-CoA Transferase from *Clostridium propionicum*

In the present example, in order to provide lactyl-CoA that is a monomer required for synthesis of PLA and PLA copolymer, propionyl-CoA transferase from *Clostridium propionicum* (CP-PCT) was used and its sequence was represented by SEQ ID NO: 3. A fragment obtained by performing PCR on chromosomal DNA of *Clostridium propionicum* using primers of SEQ ID NOs: 21 and 22 was used as CP-PCT. In this case, an NdeI site existing in wild-type CP-PCT was removed using SDM to facilitate cloning.

SEQ ID NO: 21:
5'-GGA ATT CAT GAG AAA GGT TCC CAT TAT TAC CGC AGA TGA-3'

SEQ ID NO: 22:
5'-GC TCT AGA TTA GGA CTT CAT TTC CTT CAG ACC CAT TAA GCC TTC TG-3'

Also, overlapping PCR was performed using a primer of SEQ ID NOs: 23 and 24 in order to add a SbfI/NdeI recognition site.

SEQ ID NO: 23:
5'-agg cct gca ggc gga taa caa ttt cac aca gg-3'

SEQ ID NO: 24:
5'-gcc cat atg tct aga tta gga ctt cat ttc c-3'

A pPs619C1300-ReAB vector containing phaC1$_{Ps6-19}$ 300, which is an SCL mutant of phaC1$_{Ps6-19}$ synthase, was cut with SbfI/NdeI to remove a monomer-supplying enzyme (phaA$_{RE}$ and phaB$_{RE}$) from *R. eutropha* H16, and the PCR-cloned CP-PCT gene was inserted into the SbfI/NdeI recognition site, thereby preparing a pPs619C1300-CPPCT recombinant vector.

Example 2

Preparation and Screening of a Library of a Mutant of Propionyl-CoA Transferase from *Clostridium propionicum*

As is known, when CP-PCT is highly expressed in *E. coli*, it causes serious metabolic disorder and exhibits toxicity. In general, recombinant *E. coli* were dead at the same time with addition of an inducer in an isopropyl-β-D-thio-galactoside (IPTG)-inducible protein production system using a tac promoter or T7 promoter, which is widely used to express recombinant proteins. For this reason, synthesis of PLA and PLA copolymer was performed using a constitutive expression system which weakly but continuously expressed genes with growth of microorganisms. In order to introduce random mutation into CP-PCT, pPs619C1300-CPPCT disclosed in Korean Patent Application No. 10-2006-0116234 was used as a template, and error-prone PCR was performed using primers of SEQ ID NOs: 1 and 2 under conditions of addition of Mn$^{2+}$ and the difference of concentration between dNTPs (refer to FIG. 2).

```
SEQ ID NO: 1:
5'-cgc cgg cag gcc tgc agg-3'

SEQ ID NO: 2:
5'-ggc agg tca gcc cat atg tc-3'
```

Thereafter, in order to amplify a PCR fragment including random mutation, PCR was performed under common conditions using primers of SEQ ID NOs: 1 and 2. A pPs619C1300-CPPCT vector containing phaC1$_{Ps6-19}$300, which is an SCL mutant of phaC1$_{Ps6-19}$ synthase, was cut with SbfI/NdeI to remove wild-type CP-PCT, and the amplified mutant PCR fragment was inserted into the SbfI/NdeI recognition site to produce a ligation mixture. The ligation mixture was introduced into E. coli JM109, thereby preparing a CP-PCT library with a scale of about ~10^5 (refer to FIG. 2). The prepared CP-PCT library was grown for 3 days in a polymer detection medium (a Luria Bertani (LB) agar, glucose 20 g/L, 3HB 1 g/L, Nile red 0.5 n/ml) and screened to confirm whether polymer was generated, thereby primarily selecting ~80 candidates. The candidates were grown for 4 days in a liquid medium (an LB agar, glucose 20 g/L, 3HB 1 g/L, ampicillin 100 mg/L, 37° C.) under polymer generation conditions and analyzed using florescence activated cell sorting (FACS), thereby selecting final two samples. Also, a recombinant expression vector containing the mutant was retrieved from E. coli and introduced into E. coli JM109 again to confirm polymer yield. Thus, it was confirmed that the E. coli transformed with a recombinant vector having a mutant of CP-PCT exhibited better performance than that having wild-type CP-PCT.

Example 3

Preparation of a PLA Copolymer Using a Mutant of Propionyl-CoA Transferase from *Clostridium propionicum*

Figure 2:
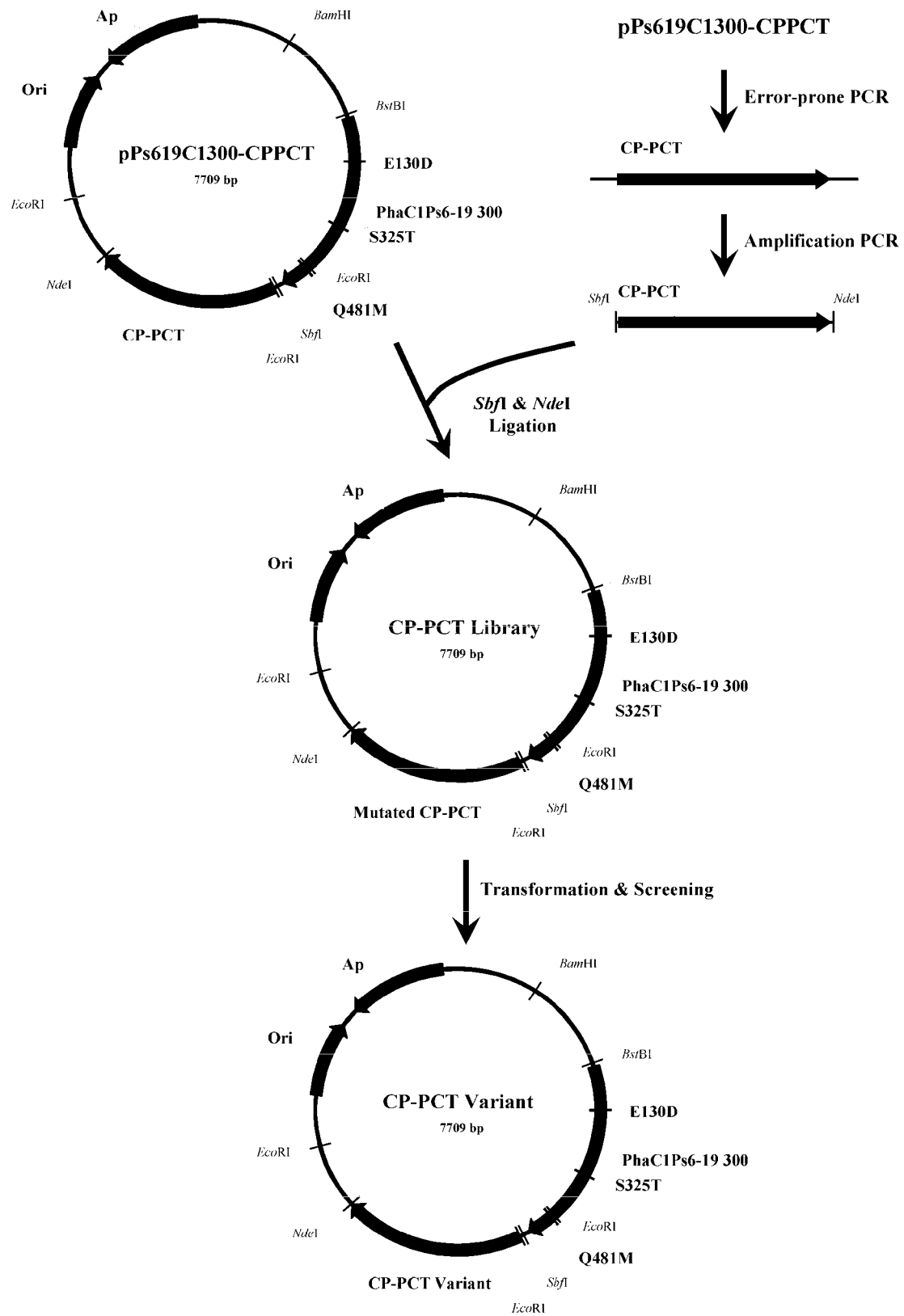
FIG. 2 is a schematic diagram of a process of preparing a recombinant expression vector containing polyhydroxyalkanoate (PHA) synthase gene from *Pseudomonas* sp. 6-19, and a mutant gene of propionyl-CoA transferase from *Clostridium propionicum*, according to an example of the present invention.

In order to quantitatively analyze activation of mutants finally selected in Example 2, E. coli JM109 transformed with the recombinant expression vector containing the mutants as shown in FIG. 2 was cultured for 4 days at a temperature of in a flask having an LB medium containing glucose (20 g/L) and 3HB (2 g/L). The cultured cell pellet was retrieved by centrifugation and dried for 24 hours in a dryer at a temperature of 100. Thereafter, gas chromatography was performed to estimate the polymer contents synthesized in cells as shown in Table 2.

TABLE 2

| Name of Strain | PLA content (w/w %) | PHB content (w/w %) |
|---|---|---|
| pPs619C1300-CPPCT/JM109 | 0.86% | 5.85% |
| CP-PCT mutant 512/JM109 | 2.19% | 12.82% |
| CP-PCT mutant 522/JM109 | 7.49% | 35.59% |

As a result of the gas chromatographic analysis, it can be seen that the recombinant expression vector containing the mutant of CP-PCT prepared according to the present invention had about two to eight times the PLA-copolymer synthetic activity of the pPs619C1300-CPPCT vector containing wild-type CP-PCT. This is because the mutant of the CP-PCT supplies polymer synthesis monomers (i.e., lactyl-CoA and 3HB-CoA) more efficiently than the wild-type CP-PCT.

In order to find out the mutant positions of the prepared CP-PCT mutants, gene sequencing was performed with respect to the CP-PCT mutants, and the results were shown in Table 3.

TABLE 3

| Recombinant vector | Nucleic acid substitution |
|---|---|
| CP-PCT mutant 512 | A1200G |
| CP-PCT mutant 522 | T78C, T669C, A1125G, T1158C |

As a result of the gene sequencing of the CP-PCT mutants, one nucleic-acid substitution occurred in the mutant 512, while four nucleic-acid substitutions occurred in the mutant 522. However, it was confirmed that all the nucleic-acid substitutions were silent mutations that cause no amino-acid substitution. That is, it was assumed that an improvement in monomer-supplying capability of the CP-PCT mutants prepared according to the present invention resulted not from an increase in activity due to amino-acid substitution of an enzyme but from a variation in the enzyme expression in E. coli. Thus, the codon usages of gene sequences of the wild-type CP-PCT and CP-PCT mutants prepared according to the present invention in typical E. coli were analyzed as shown in Table 4.

TABLE 4

|  | 78 | 669 | 1125 | 1158 | 1200 |
|---|---|---|---|---|---|
| Wild-type CP-PCT | GGT (Gly) | GGT (Gly) | AAA (Lys) | CGT (Arg) | ACA (Thr) |
|  | 24.7 | 24.7 | 33.6 | 20.9 | 7.1 |
| CP-PCT mutant 512 | GGT (Gly) | GGT (Gly) | AAA (Lys) | CGT (Arg) | ACG (Thr) |
|  | 24.7 | 24.7 | 33.6 | 20.9 | 14.4 |
| CP-PCT mutant 522 | GGC (Gly) | GGC (Gly) | AAG (Lys) | CGC (Arg) | ACA (Thr) |
|  | 29.6 | 29.6 | 10.3 | 22.0 | 7.1 |

As shown in Table 4, all the nucleic-acid substitutions except A1125G existing in the mutant 522 were advantageous for the codon usage of *E. coli*. That is, due to the nucleic-acid substitution being advantageous for the codon usage of the *E. coli*, the CP-PCT mutants prepared according to the present invention increased the expression of an activated enzyme and thus exhibited higher monomer-supplying capabilities required for production of PLA copolymers.

Example 4

Preparation of a PLA Copolymer Using a Mutant of Propionyl-CoA Transferase from *Clostridium propionicum*

Random mutagenesis was performed on the mutants (512 and 522) finally selected in Example 2, in the same manner as described in Example 2, thereby obtaining the following CP-PCT mutants 531-537 and 540.

In order to quantitatively analyze the CP-PCT mutants, *E. coli* JM109 transformed with the recombinant expression vector containing the CP-PCT mutants 531-537 and 540 was cultured for 4 days at a temperature of 30° C. in a flask having a P-rich methyl red (MR) medium containing glucose (20 g/L) and 3HB (2 g/L). The cultured cell pellet was retrieved by centrifugation and dried for 24 hours in a dryer maintained at a temperature of 100° C. Thereafter, gas chromatography was performed to estimate the contents of polymers synthesized in cells. The results of gene sequencing with respect to the CP-PCT mutants performed to find out the mutation positions of the CP-PCT mutants are shown in Table 5, and the contents of the polymers synthesized in the cells are shown in Table 6.

In the above-described experiment, P-rich MR was formed of 22 g of $KH_2PO_4$; 3 g of $(NH_4)_2HPO_4$; 0.8 g of Citrate; 0.7 g of $MgSO_4 \cdot 7H_2O$; and 5 mL of a trace metal solution per liter, and the trace metal solution was formed of 10 g of $FeSO_4 \cdot 7H_2O$; 2.25 g of $ZnSO_4 \cdot 7H_2O$; 1 g of $CuSO_4 \cdot 5H_2O$; 0.5 g of $MnSO_4 \cdot 5H_2O$; 2 g of $CaCl_2 \cdot 2H_2O$; 0.23 g of $Na_2B_4O_7 \cdot 7H_2O$; 0.1 g of $(NH_4)_6Mo_7O_{24}$; and 10 mL of HCl 35% per liter.

TABLE 5

| | Mutations | Silent Mutations |
|---|---|---|
| CpPct512 | | A1200G |
| CpPct522 | | T78C, T669C, A1125G, T1158C |
| CpPct531 | Gly335Asp | A1200G |
| CpPct532 | Ala243Thr | A1200G |
| CpPct533 | Asp65Gly | T669C, A1125G, T1158C |
| CpPct534 | Asp257Asn | A1200G |
| CpPct535 | Asp65Asn | T669C, A1125G, T1158C |
| CpPct537 | Thr199Ile | T669C, A1125G, T1158C |
| CpPct540 | Val193Ala | T78C, T669C, A1125G, T1158C |

TABLE 6

| Name | Polymer content (%) | Lac mol % | 3HB mol % |
|---|---|---|---|
| PCT (wild control) | 24.9 | 38.0 | 62.0 |
| 531 | 26.5 | 56.5 | 43.5 |
| 532 | 23.5 | 54.5 | 45.5 |
| 533 | 25.2 | 63.8 | 36.2 |
| 534 | 23.9 | 58.0 | 42.0 |
| 535 | 30.7 | 59.2 | 40.8 |
| 537 | 33.3 | 52.4 | 47.6 |
| 540 | 23.7 | 21.3 | 78.7 |

As shown in Table 6, the CP-PCT mutants prepared according to the present invention remarkably increased lactate mole % compared to wild-type CP-PCT. Also, it was confirmed that the recombinant expression vector containing the mutants 531, 533, 535, 537, and 540 exhibited better PLA-copolymer synthetic activity than the vector containing wild-type CP-PCT.

While the invention has been shown and described with reference to certain examples thereof, it will be understood by those skilled in the art that various changes in form and details may be made therein without departing from the spirit and scope of the invention as defined by the appended claims.

The invention claimed is:
1. An isolated mutant of propionyl-CoA transferase supplying lactyl-CoA, which has a gene sequence of SEQ ID NO: 3, in which T669C, A1125G and T1158C are mutated, wherein the propionyl-CoA transferase comprises
 a) a gene sequence of SEQ ID NO: 3, in which T669C, A1125G and T1158C are mutated and one mutation of the nucleic acid is further introduced to cause mutation of Asp65Gly;
 b) a gene sequence of SEQ ID NO: 3, in which T669C, A1125G and T1158C are mutated and one mutation of the nucleic acid is further introduced to cause mutation of Asp65Asn;
 c) a gene sequence of SEQ ID NO: 3, in which T669C, A1125G and T1158C are mutated and one mutation of the nucleic acid is further introduced to cause mutation of Thr199Ile; or
 d) a gene sequence of SEQ ID NO: 3, in which T78C, T669C, A1125G and T1158C are mutated and one mutation of the nucleic acid is further introduced to cause mutation of Val193Ala.

* * * * *